(12) United States Patent
Goldemann

(10) Patent No.: US 7,174,890 B2
(45) Date of Patent: Feb. 13, 2007

(54) BREATHING-CONTROLLED INHALATION DEVICE FOR DRY POWDERS

(75) Inventor: Raul Goldemann, Yeshayahu Hanavi 39/1, Modlin (IL) 71700

(73) Assignees: Angela Eckardt, Berlin (DE); Raul Goldemann, Modiin (IL); Ofer Frydling, Berlin (DE)

( * ) Notice: Subject to any disclaimer, the term of this patent is extended or adjusted under 35 U.S.C. 154(b) by 0 days.

(21) Appl. No.: 10/496,409

(22) PCT Filed: Nov. 22, 2001

(86) PCT No.: PCT/DE01/04377

§ 371 (c)(1),
(2), (4) Date: Feb. 3, 2005

(87) PCT Pub. No.: WO03/047670

PCT Pub. Date: Jun. 12, 2003

(65) Prior Publication Data

US 2005/0118111 A1    Jun. 2, 2005

(51) Int. Cl.
*A61M 15/00* (2006.01)
*A61M 16/00* (2006.01)

(52) U.S. Cl. ............................ 128/203.15; 128/203.21

(58) Field of Classification Search .......... 128/203.12, 128/203.15, 203.21, 203.23, 201.26, 204.25, 128/205.21
See application file for complete search history.

(56) References Cited

U.S. PATENT DOCUMENTS

| 4,265,236 A | 5/1981 | Pacella ................. 128/203.23 |
| 5,239,991 A | 8/1993 | Chawla et al. ......... 128/203.15 |
| 5,562,918 A | 10/1996 | Stimpson .................... 424/451 |

FOREIGN PATENT DOCUMENTS

| WO | 9622802 | 8/1996 |
| WO | 9834662 | 8/1998 |
| WO | 9853869 | 12/1998 |

*Primary Examiner*—Henry Bennett
*Assistant Examiner*—Shumaya B. Ali
(74) *Attorney, Agent, or Firm*—Baker Botts L.L.P.

(57) ABSTRACT

The invention relates to a breathing-controlled inhalation device for dry powders, having an air guide unit consisting of an essentially cylindrical body, said air guide unit comprising a flow passage provided alternately with constrictions and in each instance following enlargements, said constrictions and enlargements passing continuously one into another, and the flow passage for the air flowing through the air guide unit being of three-dimensional meander-like conformation.

19 Claims, 2 Drawing Sheets

BREATHING-CONTROLLED INHALATION DEVICE FOR DRY POWDERS

CROSS REFERENCE TO RELATED APPLICATIONS

The present application is a U.S. national stage application of International Patent Application No. PCT/DE01/04377, filed Nov. 22, 2001, published in German on Jun. 12, 2003 as PCT Publication No. WO03/047670, incorporated herein in its entirety. This application claims priority from the aforementioned International Application pursuant to 35 U.S.C. § 365. This application is also related to U.S. patent application Ser. No. 10/117,762 filed Apr. 4, 2002 based upon German application Nos. 199 48 289.6 filed Oct. 6, 1999, and 100 27 631.8 filed Jun. 6, 2000, and International Application PCT/DE00/03527 filed Oct. 6, 2000, which U.S. patent application published as U.S. patent publication No. 2002129817 A1 and issued as U.S. Pat. Ser. No. 6,729,328 B1 all of which applications are incorporated by reference herein.

BACKGROUND OF THE INVENTION

Inhalation as a gentle therapeutic method is of great importance today, primarily in the field of disorders of the respiratory passages, or for simple and fast-acting administration of medicinal drugs. A dry powder treated with medicinal drugs may be supplied to the patient's respiratory passages as a fine mist. The method of delivery during inhalation requires a complete and uniform distribution of the dry powder that is uncomplicated and rapid.

German Patent Application 199 48 289.6 discloses an apparatus that makes possible such a distribution of the dry powder by the flow-controlling structure of a simple cylindrical body in a special inhalation housing. The air guide unit disclosed is in the form of a cylindrical body, surrounded by a housing, and is not flexibly replaceable. The dry powder must be fed to a special supply chamber, before its delivery to the air guide unit. To guarantee exact dosage of the dry powder and to ensure that the dry powder does not pick up any moisture, considerable technical outlay is required of the user.

U.S. Pat. No. 5,562,918 discloses a dispenser system for the inhalation of powdered medicinal drugs by suction using respiratory air. This dispenser consists of several parts, specifically a cylindrical main body comprising closures openable by action of axial force and is provided with an intake opening and an air inlet. To achieve an adequate turbulence of the air drawn in by the dispenser, a turbine is provided in the air inlet. In the nozzle, a grid is further provided, to prevent intake of larger particles.

The dispenser disclosed in U.S. Pat. No. 5,562,918 exhibits a complicated structure, rendering it costly to produce and complicated to use. The dispenser is limited in that two or more dispensers cannot be connected to each other magazine-fashion. Although it is a prerequisite for inhalation of all powder uniformly distributed in the air, the adequate turbulence of the air taken in by the dispenser is not to be expected through the use of the disclosed dispenser.

WO A 96/22802 shows an inhaler comprising a tubular body to define an air passage, provided with closure caps and filled with a powder. The air passage may be rectangular, square, polygonal, elliptical or circular in cross-section, the cross-sectional area being smaller at the nozzle than at the opposed end. In addition, flexible segments are provided to permit adaptation to anatomical givens. In order to improve the distribution of the particles being inhaled, the inhaler may be provided with means to generate a rotation of the air. Such means may comprise spiraled depressions or ribs on the inner wall of the tubular body. This inhaler, in the simplest embodiment, is of very simple structure, but fails to achieve an adequate turbulence of the air.

An inhalation device for delivery of dry powders must be simple to use and readily available at a moment's notice. Therefore, there is a need to minimize problems by simplifying the technical structure of the inhalation device.

The object of the invention, then, is to create an inhalation device affording access in a matter of seconds by immediate readiness for use, and by a structural reduction of the elements of the device, limiting to a minimum the operating moves of the patient before, during and after the inhalation, and likewise structurally ruling out virtually any risk of trouble.

SUMMARY OF THE INVENTION

The invention relates to a breathing-controlled inhalation device for dry powders, having an air guide unit consisting of an essentially cylindrical body, said air guide unit comprising a flow passage provided alternately with constrictions and in each instance following enlargements, said constrictions and enlargements passing continuously one into another, and the flow passage for the air flowing through the air guide unit being of three-dimensional meander-like conformation.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
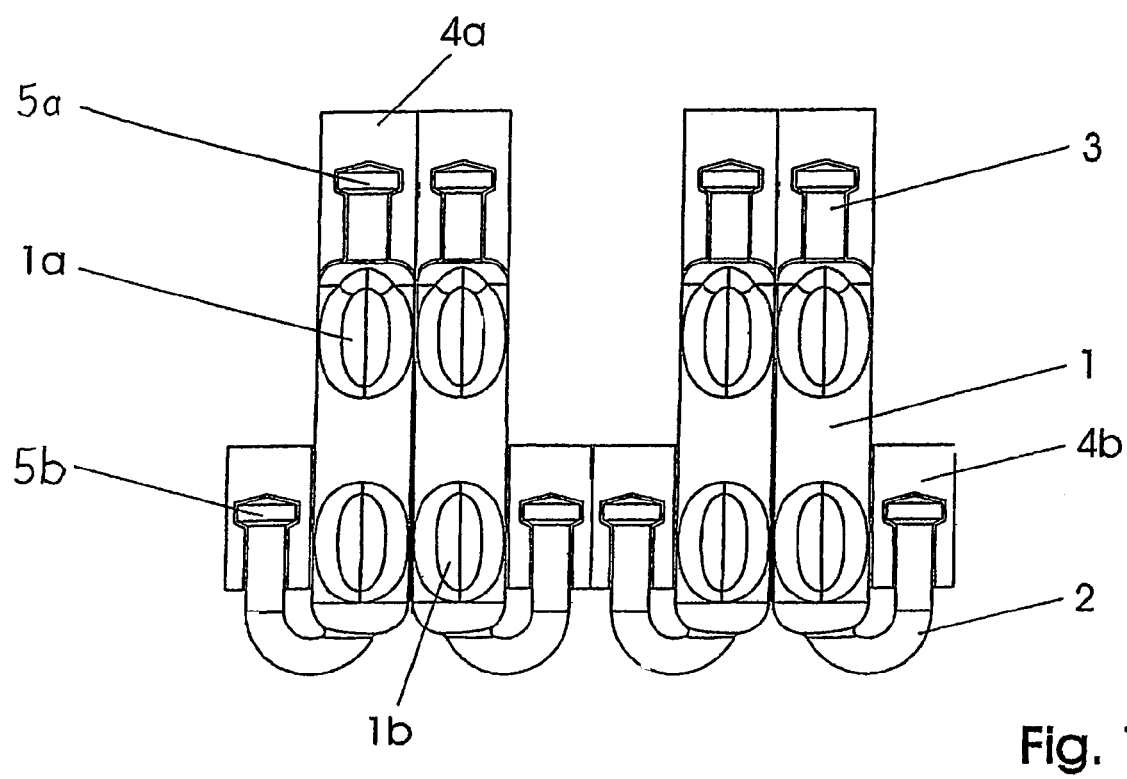
FIG. 1 shows the inhalation device in a possible magazine arrangement.

The invention relates to a breathing-controlled inhalation device for dry powders, having an air guide unit consisting of an essentially cylindrical body, said air guide unit comprising a flow passage provided alternately with constrictions and in each instance following enlargements, said constrictions and enlargements passing continuously one into another, and the flow passage for the air flowing through the air guide unit being of three-dimensional meander-like conformation.

The inhalation device of the present invention comprises a magazine of one-piece bodies of cylindrical configuration as air guide unit, each body being provided with an air inlet and an intake opening oriented in like direction and each sealed in transport condition with an authenticity closure, the bodies being directly or indirectly interconnected by way of a plurality of weak spots, and the bodies being filled with a rationed quantity of dry powder.

The presently claimed device provides an extremely economical and immediately available apparatus placed at the patient's disposal. The patient may inhale rationed active agents at need without being exposed to any risk of trouble with the inhalation device. First of all, the active agent is already contained in the magazined air guide units, readily detachable from each other. Secondly, the inhalation device itself has been technically optimized. The device according to the present invention dispenses entirely without movable parts. Therefore, the presently claimed device can be produced very economically and treated as a disposable item. In addition, the penetration of moisture is securely prevented.

The sealing of the inhalation device with authenticity closures ensures that always only the predetermined quantity of the active agent already present in the air guide unit, namely dry powder, is available.

In an embodiment of the invention, the authenticity closures can be separated without problems at prestamped weak spots. As used herein, weak spots are junctures at which various parts of the inhalation device are connected. The weak spots may be indentations or perforations in the material that form the inhalation device.

In one embodiment of the invention, the authenticity closure is fixedly connected to a flat geometrical grip part. The grip part is convenient for detaching the authenticity closure.

An another embodiment of the invention, the air inlet and the intake opening, lying in a recess of corresponding outline in the current grip part, are connected to the current grip part by way of weak spots. The grip parts are arranged in the plane of symmetry of the magazine and weak spots are provided between the current grip parts and the cylindrical bodies.

The grip parts perform the function of a geometrically symmetrical binding element between the several cylindrical bodies, directly or indirectly connected by way of weak spots. In addition, they stabilize the integrity of the authenticity closures.

By virtue of the weak spots provided in the manner specified, the cylindrical bodies can be first separated from each other, and then the intake opening and the air inlet completely freed from the grip parts.

In another embodiment of the invention, the cylindrical bodies are arranged in pairs inside the magazine, the cylindrical bodies within a pair being connected to each other by way of weak spots at the outer edges of the grip parts of the air inlet. These pairs may in turn be interconnected by weak spots at each of the outer edges of the cylindrical bodies opposed to the grip parts of the air inlet. The arrangement here chosen for the cylindrical bodies within the magazine represents an especially favorable variant connection, distinguished by a high stability and conducive, within the process of manufacture, to filling up the cylindrical bodies with the dry powder and to the subsequent steps of connection and sealing. Other variants of arrangement are conceivable.

In a preferred embodiment of the invention, the weak spots for separating the authenticity closure at the air inlet are stronger than the weak spots between air inlet and grip part and the weak spots between grip part and cylindrical body. In addition, the weak spots for separating the authenticity closure at the intake opening is stronger than the weak spots between intake opening and grip part and the weak spots between grip part and cylindrical body. This ensures that the authenticity closure will not be opened inadvertently.

In another embodiment of the invention, the weak spots between the grip part and the cylindrical body is stronger than the weak spots at the outer edge of the grip part and the weak spots at the outer edge of the cylindrical body opposed to the grip part of the air inlet. This prevents a partial or complete detachment of the grip part from the cylindrical body upon release of only a single air guide unit from the magazine, thus endangering the stabilization of the authenticity closure by the grip part.

Figure 2:
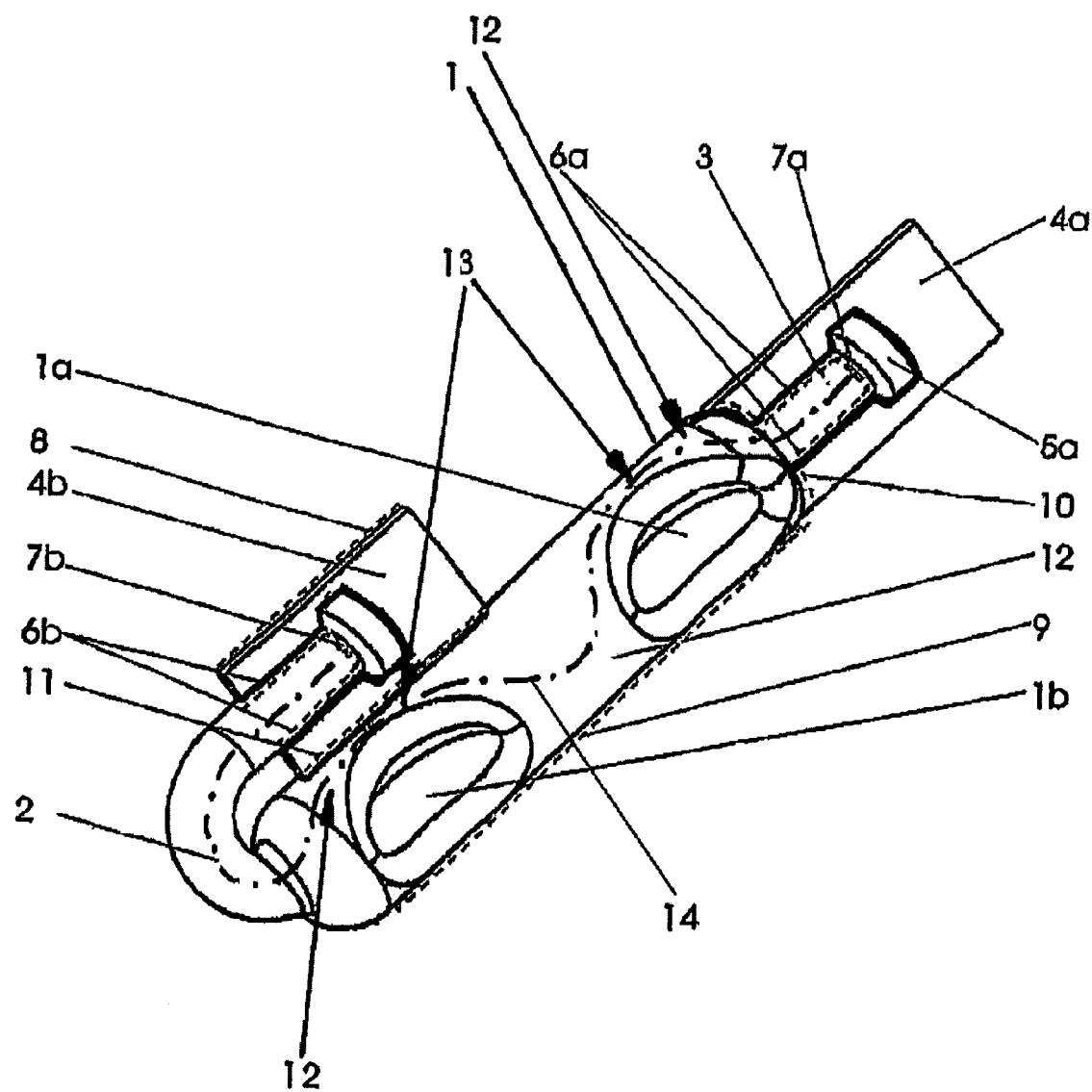
FIG. 2 shows an individual air guide unit in the form of a cylindrical body.

The invention will be further illustrated below in terms of an embodiment by way of example referred to in FIGS. 1 and 2 and is in no manner limited by the provided example. Reference to numerals in FIGS. 1 and 2 is provided in Table 1 below.

TABLE 1

| List of Reference Numerals and their corresponding descriptions | |
|---|---|
| 1 | cylindrical body |
| 1a | upper spherical segment-like depressions |
| 1b | lower spherical segment-like depressions |
| 2 | air inlet |
| 3 | intake opening |
| 4a | upper grip part |
| 4b | lower grip part |
| 5a | upper authenticity closure |
| 5b | lower authenticity closure |
| 6a | intake opening weak spots |
| 6b | air inlet weak spots |
| 7a | upper authenticity closure weak spots |
| 7b | lower authenticity closure weak spots |
| 8 | lower external grip part weak spots |
| 9 | cylindrical body weak spots |
| 10 | horizontal cylindrical body weak spots |
| 11 | lower internal grip part weak spots |

The inhalation device according to the invention consists of a plurality of cylindrical bodies (1) connected to form a chain in magazine fashion. These cylindrical bodies (1) are provided as air guide units, comprising a flow passage provided alternately with constrictions (13) and in each instance following enlargements (12), said constrictions and enlargements passing continuously one into another, and the flow passage for the air flowing through the air guide unit having a three-dimensional meander-like (i.e., a crooked or winding) conformation (i.e. structure, shape, form, configuration, or contour). The cylindrical body (1) is provided for this purpose with spherical depressions (1a) and (1b), extending from mutually opposed walls of the cylindrical body (1) into the flow passage (14).

The patient can at need take from the magazine a single air guide unit with a pre-portioned quantity of dry powder treated with medicinal drugs, or a medicinal drug in the form of dry powder. The individual air guide units in the form of the cylindrical bodies (1) are connected to each other directly or indirectly by way of flat lower grip parts (4b) by pre-stamped weak spots (8; lower external grip part weak spots) and (9; cylindrical body weak spots), so that the required air guide unit can be broken out of the magazine.

As favorable to the stabilization of the device, important in transport, an arrangement has been found such that the cylindrical bodies (1) are arranged in the magazine in pairs, the cylindrical bodies (1) within a pair being connected to each other at the outer edges of the lower grip part (4b) of the air inlets (2). These pairs are in turn connected, again by weak spots (8; lower external grip part weak spots) and (9; cylindrical body weak spots), at each outer edge of the cylindrical body (1) opposed to the lower grip parts (4b) of the air inlet (2).

The cylindrical bodies are directly or indirectly connected one to another by way of weak spots (8; lower external grip part weak spots) and (9; cylindrical body weak spots) in that each cylindrical body is provided with an air inlet (2) and an intake opening (3) oriented in like direction and, in transport condition, each sealed with an authenticity closure (5*a*; upper) and (5*b*; lower).

The upper and lower authenticity closures (5*a* and 5*b*) may be connected to the air inlet (2) and the intake opening (3) by way of a weak spots (7*a*; upper authenticity closure weak spots and 7*b*; lower authenticity closure weak spots).

The upper and lower authenticity closures (5*a* and 5*b*) may each be fixedly connected to flat upper and lower geometrical grip parts (4*a* and 4*b*). The upper and lower grip parts (4*a* and 4*b*) may be arranged in the plane of symmetry of the magazine.

The air inlet (2) of the device, lying in a recess of the lower grip part (4*b*) matching the outline of the air inlet (2), may be connected to the lower grip part (4*b*) by way of air inlet weak spots (6*b*), and furthermore there is a connection in the form of a weak spots (11; lower internal grip part weak spots) between the lower grip part and the cylindrical body.

Since the weak spots (7*b*; lower authenticity closure weak spots) for detaching the lower authenticity closure (5*b*) at the air inlet (2) is stronger than the weak spots (6*b*; air inlet weak spots) between air inlet (2) and lower grip part (4*b*) and the weak spots (11; lower internal grip part weak spots) between lower grip part (4*b*) and the cylindrical body (1), and furthermore the weak spots (7*a*; upper authenticity closure weak spots) for detaching the upper authenticity closure (5*a*) at the intake opening (3) is stronger than the weak spots (6*a*; intake opening weak spots) between intake opening (3) and upper grip part (4*a*) and the weak spots (10; horizontal cylindrical body weak spots) between the upper grip part (4*a*) and cylindrical body (1), it is ensured that the upper authenticity closure (5*a*) is not opened inadvertently.

An inadvertent release of the lower grip part (4*b*), and hence an endangerment of the stabilization of the lower authenticity closure (5*b*) is further prevented in that the weak spots (11; lower internal grip part weak spots) between the lower grip part (4*b*) and cylindrical body (1) is stronger than the weak spots at the outer edge of the lower grip part (8; lower external grip part weak spots) and the weak spots (9; cylindrical body weak spots) at the outer edge of the cylindrical body (1) opposed to the lower grip part (4*b*) of the air inlet (2).

In order to be able to inhale the quantity of dry powder contained by the air guide unit, the upper and lower authenticity closures (5*a*) and (5*b*) located at an air inlet (2) and intake opening (3) and likewise connected to these by way of weak spots (7*a*; upper authenticity closure weak spots) and (7*b*; lower authenticity closure weak spots) are detached by means of the upper and lower grip parts (4*a*) and (4*b*), the grip parts being completely eliminable from the cylindrical bodies by breaking up corresponding weak spots (6*a*, 6*b*, 10 and 11), and the inhalation device thereby finally put into the condition ready for use. Thereupon, the intake opening (3) of the inhalation device can be brought to the mouth and air taken in, or inhaled. Upon intake of the air flowing in by way of the air inlet (2), the special meander-like conformation of the cylindrical body (1) as described arising from alternating constrictions and enlargements results in an optimal distribution of the dry powder particles treated with the active substance, in that the air passing through is caused to circulate in a special manner. Since the intake opening (3) and the air inlet (2) are oriented alike, i.e. upward, and the patient when inhaling will incline his head by hardly more than 90 degrees, unintentional escape of the dry powder is not possible.

Various references, patents, publications, product descriptions, etc., are cited throughout this specification, the disclosures of which are incorporated herein by reference in their entireties for all purposes.

The invention claimed is:

1. A breathing-controlled inhalation device for dry powders, having an air guide unit consisting essentially of a cylindrical body, said air guide unit comprising a flow passage alternately provided with constrictions and in each instance following enlargements, said constrictions and enlargements passing continuously one into another, so that the flow passage is of three-dimensional meander-like conformation, wherein at least two cylindrical bodies connected to each other in a magazine-fashion are provided as air guide units, the cylindrical bodies being directly or indirectly connected one to another by way of weak spots in that each cylindrical body is provided with an air inlet and an intake opening oriented in like direction and, in transport condition, each sealed with an authenticity closure, wherein the intake opening is sealed with an upper authenticity closure and the an air inlet is sealed with a lower authenticity closure, wherein the upper authenticity closure is fixedly connected to a flat geometrical upper grip part and the lower authenticity closure is fixedly connected to a flat geometrical lower grip part, and wherein the cylindrical bodies are filled with a rationed quantity of dry powder.

2. The breathing-controlled inhalation device according to claim 1, wherein the upper and lower grip parts are arranged in the plane of symmetry of the magazine.

3. The breathing-controlled inhalation device according to claim 1, wherein the air inlet, lying in a recess of the lower grip part matching the outline of the air inlet, is connected to the lower grip part by way of air inlet weak spots, and the lower grip part is connected to the cylindrical body by lower internal grip part weak spots.

4. The breathing-controlled inhalation device according to claim 2, wherein the air inlet, lying in a recess of the lower grip part matching the outline of the air inlet, is connected to the lower grip part by way of air inlet weak spots, and the lower grip part is connected to the cylindrical body by lower internal grip part weak spots.

5. The breathing-controlled inhalation device according to claim 1, wherein the intake opening, lying in a recess of the upper grip part matching the outline of the intake opening, is connected to the upper grip part by way of intake opening weak spots, and the upper grip part is connected to the cylindrical body by horizontal cylindrical body weak spots.

6. The breathing-controlled inhalation device according to claim 2, wherein the intake opening, lying in a recess of the upper grip part matching the outline of the intake opening, is connected to the upper grip part by way of intake opening weak spots, and the upper grip part is connected to the cylindrical body by horizontal cylindrical body weak spots.

7. The breathing-controlled inhalation device according to claim 1, wherein the cylindrical bodies are arranged in pairs within the magazine, the cylindrical bodies being connected to each other by way of lower external grip part weak spots found at the outer edges of the lower grip part of the air inlets.

8. The breathing-controlled inhalation device according to claim 2, wherein the cylindrical bodies are arranged in pairs within the magazine, the cylindrical bodies being connected to each other by way of lower external grip part weak spots found at the outer edges of the lower grip part of the air inlets.

9. The breathing-controlled inhalation device according to claim 7 or 8, wherein the pairs are connected to each other in each instance by way of cylindrical body weak spots found at the outer edges of the cylindrical bodies opposed to the lower grip parts of the air inlet.

10. The breathing-controlled inhalation device according to claim 8, wherein the pairs are connected to each other in each instance by way of cylindrical body weak spots found at the outer edges of the cylindrical bodies opposed to the lower grip parts of the air inlet.

11. The breathing-controlled inhalation device according to claim 3, wherein horizontal lower authenticity closure weak spots for detaching the lower authenticity closure at the air inlet is stronger than (1) the lower internal grip part weak spots located between air inlet and lower grip part and (2) lower internal grip part weak spots found between the lower grip part and cylindrical body.

12. The breathing-controlled inhalation device according to claim 4, wherein horizontal lower authenticity closure weak spots for detaching the lower authenticity closure at the air inlet is stronger than (1) the lower internal grip part weak spots located between air inlet and lower grip part and (2) lower internal grip part weak spots found between the lower grip part and cylindrical body.

13. The breathing-controlled inhalation device according to claim 5, wherein upper authenticity closure weak spots for detaching the upper authenticity closure at the intake opening is stronger than (1) intake opening weak spots found between intake opening and upper grip part and (2) horizontal cylindrical body weak spots found between the upper grip part and cylindrical body.

14. The breathing-controlled inhalation device according to claim 6, wherein upper authenticity closure weak spots for detaching the upper authenticity closure at the intake opening is stronger than (1) intake opening weak spots found between intake opening and upper grip part and (2) horizontal cylindrical body weak spots found between the upper grip part and cylindrical body.

15. The breathing-controlled inhalation device according to claim 11, wherein lower internal grip part weak spots found between the lower grip part and cylindrical body is stronger than (1) the lower external grip part weak spots found at the outer edge of the lower grip part and (2) the cylindrical body weak spots at the outer edge of the cylindrical body opposed to the lower grip part of the air inlet.

16. The breathing-controlled inhalation device according to claim 12, wherein lower internal grip part weak spots found between the lower grip part and cylindrical body is stronger than (1) the lower external grip part weak spots found at the outer edge of the lower grip part and (2) the cylindrical body weak spots at the outer edge of the cylindrical body opposed to the lower grip part of the air inlet.

17. The breathing-controlled inhalation device according to claim 13, wherein lower internal grip part weak spots found between the lower grip part and cylindrical body is stronger than (1) the lower external grip part weak spots found at the outer edge of the lower grip part and (2) the cylindrical body weak spots at the outer edge of the cylindrical body opposed to the lower grip part of the air inlet.

18. The breathing-controlled inhalation device according to claim 14, wherein lower internal grip part weak spots found between the lower grip part and cylindrical body is stronger than (1) the lower external grip part weak spots found at the outer edge of the lower grip part and (2) the cylindrical body weak spots at the outer edge of the cylindrical body opposed to the lower grip part of the air inlet.

19. The breathing-controlled inhalation device according to claim 1, wherein the lower authenticity closure is connected to the air inlet by way of lower authenticity closure weak spots and the upper authenticity closure is connected to the intake opening by way of upper authenticity closure weak spots.

\* \* \* \* \*